US010624801B2

(12) United States Patent
Mahe (10) Patent No.: US 10,624,801 B2
(45) Date of Patent: Apr. 21, 2020

(54) LOOPED LAYER OR STRIP INCLUDING DIFFERENTIAL ATTACHMENT AREAS AND NAPPY COMPRISING SUCH A LAYER

(71) Applicant: APLIX, Le Cellier (FR)

(72) Inventor: Anthony Bertrand Mahe, Thouaré sur Loire (FR)

(73) Assignee: APLIX, Le Cellier (FR)

( * ) Notice: Subject to any disclaimer, the term of this patent is extended or adjusted under 35 U.S.C. 154(b) by 712 days.

(21) Appl. No.: 15/301,964

(22) PCT Filed: Apr. 7, 2015

(86) PCT No.: PCT/EP2015/057440
§ 371 (c)(1),
(2) Date: Oct. 5, 2016

(87) PCT Pub. No.: WO2015/155149
PCT Pub. Date: Oct. 15, 2015

(65) Prior Publication Data
US 2017/0105890 A1    Apr. 20, 2017

(30) Foreign Application Priority Data
Apr. 8, 2014   (FR) .................................... 14 00850

(51) Int. Cl.
*A61F 13/62*     (2006.01)
*B32B 7/03*      (2019.01)
(Continued)

(52) U.S. Cl.
CPC ............ *A61F 13/627* (2013.01); *A61F 13/49* (2013.01); *A61F 13/51121* (2013.01);
(Continued)

(58) Field of Classification Search
CPC ...... A61F 13/62; A61F 13/622; A61F 13/627; A44B 18/0011; A44B 18/0034;
(Continued)

(56) References Cited

U.S. PATENT DOCUMENTS 5,032,122 A * 7/1991 Noel .................. A44B 18/0011
24/442
6,332,250 B1 * 12/2001 Igaue ................. A44B 18/0011
24/445
(Continued)

FOREIGN PATENT DOCUMENTS

EP         0 800 808 A1    10/1997

*Primary Examiner* — Catharine L Anderson
(74) *Attorney, Agent, or Firm* — Renner Kenner Greive Bobak Taylor & Weber (57) ABSTRACT

The invention relates to a looped layer in the form of a laminate including an inner supporting element (1), for example a non-woven fabric or a plastic film, and a plurality of fibres and/or filaments (3) attached to the outer surface of the supporting element so as to form loops for engaging with hooks, the attachment being carried out in a attachment region, while in at least one other so-called looped region the filaments and/or fibres are not attached to the supporting element so as to form loops, characterised in that at least in one area (5) of at least one attachment region the attachment is only carried out in a partial manner, while at least in one other area (4) of at least one attachment region the attachment is carried out in a complete manner.

14 Claims, 5 Drawing Sheets

(51) Int. Cl.
| | |
|---|---|
| *B32B 7/05* | (2019.01) |
| *B32B 5/02* | (2006.01) |
| *B32B 5/12* | (2006.01) |
| *B32B 5/26* | (2006.01) |
| *D04H 1/45* | (2006.01) |
| *D04H 11/08* | (2006.01) |
| *B32B 5/14* | (2006.01) |
| *B32B 27/12* | (2006.01) |
| *A61F 13/49* | (2006.01) |
| *A61F 13/511* | (2006.01) |
| *A61F 13/84* | (2006.01) |

(52) U.S. Cl.
CPC ............... *B32B 5/022* (2013.01); *B32B 5/12* (2013.01); *B32B 5/142* (2013.01); *B32B 5/147* (2013.01); *B32B 5/26* (2013.01); *B32B 7/03* (2019.01); *B32B 7/05* (2019.01); *B32B 27/12* (2013.01); *D04H 1/45* (2013.01); *D04H 11/08* (2013.01); *A61F 2013/8497* (2013.01); *B32B 2307/542* (2013.01); *B32B 2307/75* (2013.01); *B32B 2555/02* (2013.01)

(58) Field of Classification Search
CPC ............ A44B 18/0057; A44B 18/0069; A44B 18/0073; D04H 1/45; D04H 11/08
See application file for complete search history.

(56) References Cited

U.S. PATENT DOCUMENTS

| | | | |
|---|---|---|---|
| 6,589,638 B1 * | 7/2003 | McCormack | A44B 18/0011 428/198 |
| 2004/0178544 A1 | 9/2004 | Jackson et al. | |
| 2009/0068393 A1 | 3/2009 | Homolle et al. | |

\* cited by examiner

LOOPED LAYER OR STRIP INCLUDING DIFFERENTIAL ATTACHMENT AREAS AND NAPPY COMPRISING SUCH A LAYER

TECHNICAL DOMAIN

The present invention relates to a layer or strip comprising loops, in the form of a laminate, for forming the loop part of a self-fastening hook and loop system, in particular for diapers and in particular for forming a band disposed in the front part of the diaper in a central position on the belt, the band classically called the "landing zone", to enable closure of the belt of the diaper by means of the attachment with hooks emanating from legs disposed in parts of lateral ends of the rear part of the diaper.

In general, this layer comprises on the one hand a support element, classically a non-woven fabric or a thermoplastic film, onto an external surface of which are printed, by applying a layer of ink, patterns or designs, in particular in view of distinguishing this area called the "landing zone" (landing zone for the hooks) from the rest of the item of clothing so as to indicate to the user the functional sealing zone, i.e. the zone in which the hooks have to be applied in order to bring about engagement, and on the other hand an element with loops secured to the support element.

BACKGROUND TO THE INVENTION

It is already known from the prior art to use a knit as a looped element. In order to secure the knit to its support it is necessary to execute numerous steps which are long and tedious and which require a great deal of precision so as to not adhere the loops to the support and to destroy their ability to engage. This does not facilitate large-scale production in a domain where this is, however, particularly sought, namely that of disposable diapers.

This is why the principle has been developed consisting of replacing the looped knit with a looped non-woven fabric.

However, a number of criteria are sought for this non-woven fabric, namely it is desirable for the hooks to be able to engage here easily and in particular to give the user the impression that they engage easily and provide high-performance and/or satisfactory engagement in the eyes of the user, at the same time, however, ensuring good visibility of the design (which can be seen by the user through the loop element), as well as a soft and pleasant touch quality. Finally, it is desirable to reduce as far as possible the weight of the landing zone in view of reducing the cost of the product and of limiting its impact upon the environment after it has been used.

However, reducing the weight of the landing zone involves in particular the non-woven fabric with loops having to be fairly lightweight, and this is beneficial in terms of being able to see through it. However, these two criteria are by all means met, but then mean that the number of loops, and in particular the number of potential engagements, is reduced such that resistance to opening by peeling away is less good, and in particular the appreciation felt by the user as regards the quality of engagement is less good.

Also known from US 2004/0178544 is a composite comprising an elastic polymeric structure that is welded in a previous step to a non-woven fabric in a trellis welding pattern. This composite is intended to be used in diapers in order to form an elastic connection between the legs with hooks and the diaper, the hooks, for sealing the diaper, engaging with a looped element disposed on the front part of the belt of the diaper, the elastic composite providing the elastic hold of the closure of the diaper achieved by the action of the hooks in the looped element, the latter being distinct from the elastic composite. In order to provide the composite with elasticity, after welding the non-woven fabric to the polymeric structure the composite is stretched in a direction parallel to the plane of the structure, the effect of which is to unsolder the non-woven fabric from the polymeric structure along the weld beads parallel to the direction of stretching so that a final welded composite is obtained only along the beads of the trellis perpendicular to the direction of stretching (with a constant welding thickness, the weld at the intersections with the horizontal beads unsoldered by the stretching having been partially unsoldered from their part corresponding to the unsoldered weld beads parallel to the direction of stretching), and so this provides the composite with elasticity in the direction of stretching.

Also known from EP 0800808 is a diaper that has a self-fastening hook and loop closure, the looped element (landing zone) being disposed on the front part of the diaper on the belt and legs with hooks emanating from the edges of the rear part of the diaper in order to engage in the looped element in order to seal the diaper. The non-woven fabric with loops comprises a mixture of two types of fiber. The fibers of the first type are joined strongly to one another. The fibers of the second type are joined to one another just as strongly. The fibers of both types are joined weakly to one another. The network of fibers of the first type forming the looped element is joined to the network of fibers of the second type by the weld points that have low, but therefore constant, strength and vice versa.

OBJECT AND SUMMARY OF THE INVENTION

The object of the present invention is to overcome the disadvantages of the prior art by proposing a looped layer or strip in the form of a laminate, intended in particular to be used as a landing zone in a diaper and which, although being able to be lightweight and so cheap to produce and allowing good visibility of the design through the non-woven fabric with loops, makes it possible to obtain a good hold of the hooks and in particular to give the user the sense of a robust closure.

According to the invention, a looped layer or strip in the form of a laminate including an internal support element, for example a non-woven fabric or a plastic film, and a plurality of fibers and/or filaments secured to the external face of the support element so as to form loops for engaging with hooks, the attachment being carried out in at least one attachment region, while in at least one other so-called looped region the filaments and/or fibers are not secured to the support element so as to thus form loops, is characterized in that at in least one zone of the at least one attachment region the attachment is only made in a partial manner, while in at least one other zone of the at least one attachment region the attachment is carried out in a complete manner.

According to the present invention, "securing carried out in a partial manner" is understood to mean attachment, in particular by fusion, in particular calendering, which is such that when a hook penetrates into one or more of the loops of the set of filaments with loops and applies normal peeling away traction, the hook/loop engagement is associated at least partly with partial disconnection of the partial attachment zone of the support element so as to thus enlarge the loop or loops with which the hook is engaging. At the same time, "complete attachment zone" is understood to mean an attachment zone which is such that when a hook penetrates into one or more loops formed by one or more filaments or fibers of the looped element and exerts normal peeling away traction, the entire attachment zone does not separate from the support element.

According to the invention, "normal" peeling away traction is understood to mean the traction force resulting from the action of a person with average strength who introduces a leg with hooks with normal dimensions for a diaper or an incontinence pad for adults and who pulls towards him or her the element with hooks after having introduced a hook into the loops of the landing zone element in order to ensure that engagement has taken place.

In particular, a normal force is considered by the person skilled in the art to be a force of between 2.2 and 13 Newtons (N) applied over a distance of 25.4 mm (1 inch). The method currently used is measuring resistance at the opening at 180° of an assembled hook/landing zone pairing. A strip of hooks that is 13 mm wide and 25.4 mm long assembled over an 80 g/m² paper support with a width of 25.4 mm is pressed onto a sample of the landing zone with dimensions of 50 mm×50 mm with a single 2 kg roller, the relative orientations of the products being identical to those used on the diaper. Traction of 1 kg is then applied for 10 seconds to the hook support so as to simulate the sealing of a diaper, in particular of a diaper that has elastic flaps. The paper supporting the hook is then inserted into the upper mobile jaw of a traction frame of the Synergie 200H type made by MTS System equipped with a 100 N dynamometric cell and the landing zone is inserted into the lower jaw. The distance between the two jaws is 50 mm. In order to measure the opening force, the upper part of the frame then executes translation from the bottom to the top at a constant speed of 305 mm/min. One then takes the value of the maximum force supplied by the machine possibly as well as the energy value corresponding to the area below the surface of the curve taken over the first 13 millimeters of the travel of the traction frame.

In order to bring about the partial disconnection of an attachment zone according to the invention, the force required for this disconnection is less than the normal force defined above.

By thus providing two types of attachment in different zones of the attachment regions between the support element and the filaments forming the loops, whether complete or partial, one substantially increases the engaging efficiency of the self-fastening system achieved with a non-woven fabric comprising small loops defined to satisfy the general appearance (visual appearance) of the product prior to use, but too small to obtain the desired performance using a landing zone that only has complete welds. One also increases the impression of solidity of the engagement gained by the user. Moreover, one reduces the formation of free filaments/fibers formed by open loops.

Preferably, at least one layer of printing ink intended to form a pattern or patterns or designs is deposited on the support element.

According to one preferred embodiment of the invention, the complete and partial attachments are achieved by welding, in particular by calendering.

When the attachments are made by calendering, the hold is ensured by interdiffusion of the molecules of the fibers/filaments and of the support. The effect of calendering is to pass the fibers/filaments and the internal support between two cylinders, at least one of them comprising a plurality of protrusions and at least one of them being heated. The protrusions make it possible to press the fibers/filaments against one another and to create the attachment zones.

When the weld is made completely, the plurality of fibers/filaments is crushed against the support so that one can no longer consider each fiber/element to be independent elements. The fibers and filaments are welded to one another and to the support.

In order to characterize the differential weld of the non-woven fabric one can define the following weld ratio:

$$RS=(1-\text{compactness of the partial weld})/(1<\text{compactness of the complete weld})$$

The density of the void (i.e. without any material) present in the partial weld being equal to 1−compactness of the partial weld, and the density of the void present in the complete weld being equal to 1−compactness of the complete weld.

Preferably, the ratio of the weld Rs is greater than 1.5, more particularly greater than 2.5 and even more preferably greater than 5, in particular 10, even 100 or more.

In particular, complete attachment is attachment such that the material obtained at the attachment zone as a volume fraction or compactness greater than 99%, whereas the material obtained at a partial attachment zone has a volume fraction or compactness less than 99%.

The volume fraction can be measured in particular by 3D scanning with X rays of the attachment zone in question. In order to take the measurement, one takes as the measurement zone (preferably with dimensions of 0.2 mm×0.2 mm up to 0.5 mm×0.5 mm) the zone where the fibers/filaments are joined to the support. One can remove 10%, preferably 7.5%, even more preferably 5% from either side of the zone in question so as to not have any side effect.

Preferably, the test is carried out at the centre of a homogeneous weld zone.

Thus, the filaments that are only partially welded are not totally destroyed by the calendering and keep a certain integrity in the partial attachment zones which is such that when traction is applied to the filament at points where it has not been welded, the weld partially "lets go", thus increasing the useful opening of the filament for the hook and thus increasing traction and in particular the sense of engagement. One understands the partial weld "lets go" to mean that at least some, preferably all of the filaments of the partial weld in contact with the support are disconnected or detached from the support.

According to one preferred embodiment of the invention, the plurality of fibers and/or filaments forming the loops are consolidated into at least one non-woven fabric.

According to one preferred embodiment of the invention, the support element is formed by at least one non-woven fabric.

According to one preferred embodiment of the invention, the attachments, in particular welds, are made in regions in the form of strips extending in the CD direction of the laminate, in particular parallel to one another, the complete and partial attachment zones being produced alternately along a strip in the CD direction.

According to another embodiment, the complete and partial attachment zones are produced so as to alternate both in the CD direction along a given strip and in the MD direction of a strip to an adjacent strip.

According to another embodiment, the partial and complete attachment zones are made alternately in the MD direction of a strip to an adjacent strip.

According to another embodiment, the partial attachment zones are made in the form of a semi-circle of which the diameter is contiguous to a loop zone.

Preferably, the layer exhibits a weld differential greater than 1.5.

The present invention also relates to a diaper comprising a strip or a layer according to the invention, and in particular the layer or the strip forms the landing zone of the diaper.

The present invention also relates to a self-fastening closure system comprising on the one hand an element with hooks and on the other hand an element with loops, the loop element comprising a strip or a layer according to the invention, in particular a self-fastening closure system for a diaper. The loop element forms the landing zone of the diaper, while the hook element forms a leg with hooks emanating from an edge of the diaper, the arrangement being such that the engagement of the hooks of the hook element with the loops of the landing zone provide closure and keep the diaper in position on the user.

BRIEF DESCRIPTION OF THE DRAWINGS

In the following embodiments are described purely as an illustration and referring to the drawings in which:

FIGS. 1 and 1B are diagrams in longitudinal section of a laminate according to the invention illustrating the principle of the invention, FIG. 1A showing the state when a hook is introduced into a loop, while FIG. 1B shows the state once the hook has applied "normal" upwards traction;

DETAILED DESCRIPTION OF EMBODIMENTS

Figure 1A:
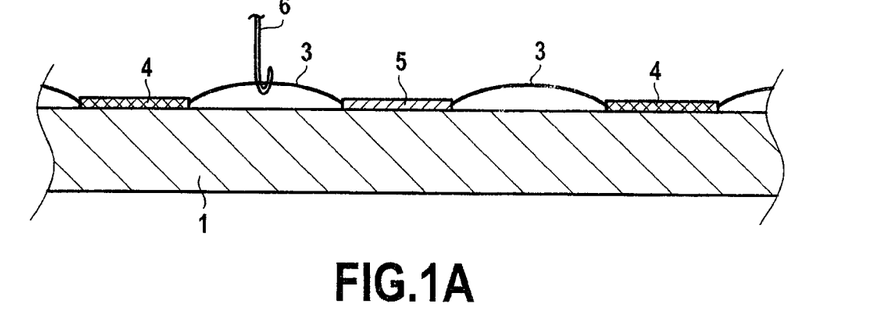
Figure 1B:
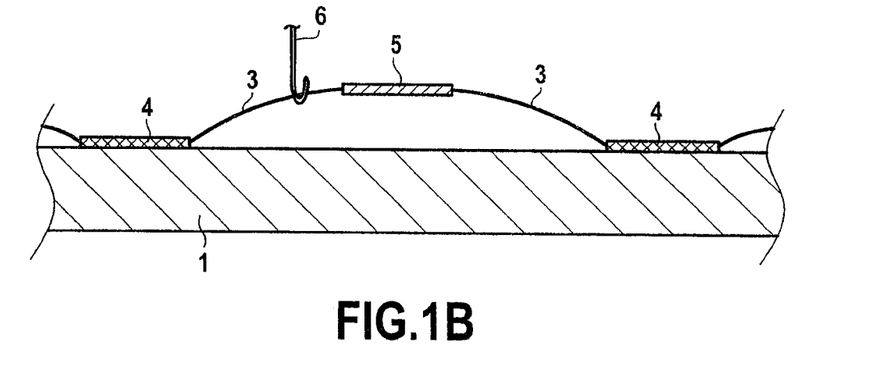

FIGS. 1A and 1B show a laminate according to the invention. The laminate comprises a base element in the form of a non-woven fabric 1 that has a lower face in the figure corresponding to the internal face intended to be located on the side of the body of the user of the diaper in a case where it is used as a landing zone and which comprises on its opposite face, which is the upper face in the figure, and so external with respect to the body of the user of the diaper, printed patterns intended to be seen from the outside and filaments and/or fibers 3 forming loops being secured by welding in weld regions 4, 5 to the non-woven fabric 1.

Figure 1C:
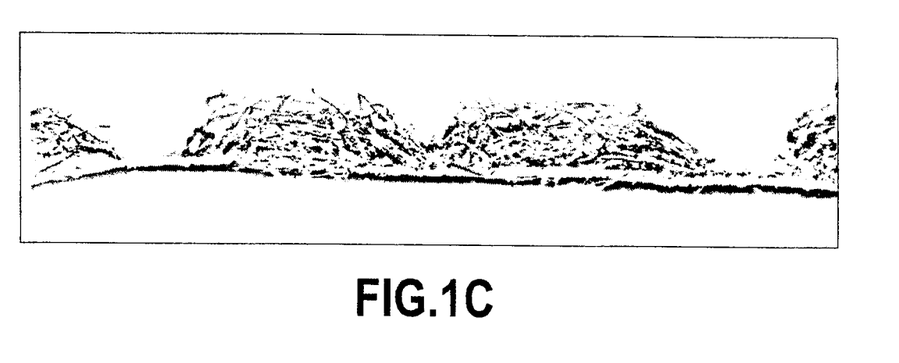
FIG. 1C is a more detailed side view of the laminate of FIG. 1A, without the hook.

In FIGS. 1A and 1B, filaments and/or fibers 3 are shown diagrammatically and form in reality a network of filaments and/or fibers as shown in FIG. 1C.

In FIGS. 1A and 1B, which are diagrammatic sectional views, one can see that the weld regions comprise two different types of weld, namely complete weld zones 4 extending in the length direction, i.e. perpendicular to the figure and which are shown by cross-hatched lines, and partial weld zones 5 which are shown by hatched lines. The laminate thus produces loops which can engage with hooks in order to provide attachment by means of a self-fastening hook and loop system, in particular for a diaper, the laminate being disposed in the central zone of the front part of the diaper on the belt, while the hooks emanate from legs disposed at the lateral ends of the rear part of the diaper, also on the belt. However, it should be noted that without straying from the framework of the invention, one could make provision for the laminate with loops to be disposed in the rear part and for the hooks to be disposed in the central part of the belt of the front part of the diaper.

Loops are understood to mean a filament and/or a fiber that comprises two ends, each one joined to the support at a respective point of the support or at a same point of the support. A loop can also be formed from a number of filaments or fibers that are joined to one another and of which at least two are joined to the support at one point or at two respective distinct points.

The two partial and complete weld zones are therefore different, and in particular the partial weld zone can detach from the supporting non-woven fabric 1 by the action of a traction force of a hook 6 that penetrates into an adjacent loop of a partial weld zone 5. One thus arrives at the situation shown in FIG. 1B. As can be seen, the complete weld zones 4 have not been separated from the non-woven fabric 1 by the action of the hook 6. On the other hand, the partial weld zone 5 has detached from the non-woven fabric 1 by the action of the hook 6 and one now thus obtains a loop with greater dimensions made up of two filaments 3 and of the zone 5 which also comprises the continuity of the same filaments.

Obviously, this effect is obtained for a so-called normal traction force of the hook. If one applies a very high traction force, the arrangement is such that the filaments break before the complete welds. For a normal traction corresponding to a traction exerted by a person with normal strength using a diaper in the normal way, the partial weld 5 will give way before the filaments 3 break and will thus produce a large loop.

In particular, in order to define whether this is a partial weld or a complete weld, one notes the volume fraction of the material contained in the weld zone that one wishes to assess. A complete weld is considered to be a weld of which the molecules of the filaments and/or fibers have been completely mixed so as to lose their dimensional integrity, and this is manifested by a passage, at the level where the weld is made, of a pile of fibers in the case of a partial weld to a mass of compact material in the case of a complete weld.

A partial weld zone will have great porosity to air, to liquid or the like and a volume fraction or compactness well below 100% and in particular well below that of a complete weld zone of which the volume fraction is close to 100%.

In the example of FIGS. 1A and 1B, the user makes the hooks penetrate into the loops so as to ensure that the diaper is sealed. Upon opening, the user pulls the hook zone towards him or her and thus exerts a force greater than the force required to disconnect the partial welds from the support. Thus, the loops are enlarged and enable one to obtain a normal opening force greater than a similar laminate comprising purely complete welds 3 and 4. For example, one obtains here an opening force measured at 4.5 N for a laminate only with complete welds, and 5.5 N for the laminate with a double complete and partial weld.

In particular, the respectively complete and partial welds are made differently and in particular with a different calendering pressure. In order to do this, in particular one can either produce patterns on the calendering rollers which are different depending upon whether one wishes to produce a complete calendering zone or a partial calendering zone. One can also provide two calendering rollers in succession, one for implementing first partial calendering with a low calendering force on all of the weld zones and then a second calendering roller in order to finish the complete calendering in the zones where one wishes the calendering to be complete, while the partial calendering zones are not affected by the second calendering roller. It should be noted that the opposite of these steps is also possible, and that the calendering zones of the first step are not affected by the second calendering roller.

One can also initially calender the web of fibers and/or filaments and then calender this web on the support. The previously calendered zones of the web then create partial attachment zones when they are calendered on the support, the pressure applied to the previous weld zone during assembly being lower.

In particular in order to determine whether a calendering zone is a partial calendering zone or a complete calendering zone, X-ray scanning of the weld zone is implemented in order to recreate the volume of material contained on the basis of different cross-sections.

FIGS. 2A, 2B, 2C, 2D, 2E, 2F and 2G show various possible embodiments for producing the laminate with loops with differential welds according to the principle of the invention.

Figure 2A:
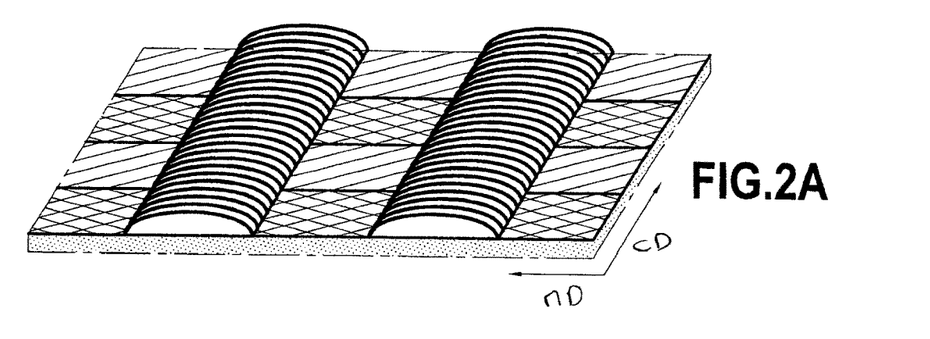
FIGS. 2A, 2B, 2C, 2D, 2E and 2F show diagrammatically laminates according to the invention in perspective according to various embodiments.

Thus, in FIG. 2A the weld regions form strips extending in the CD direction alternating with zones in which the filaments are not welded to form loops with respect to the support element 1. Furthermore, as shown in the figures, in each weld attachment region in the form of a strip, complete weld zones 4 alternate with partial weld zones 5 in the CD direction. As shown, each zone has substantially the same longitudinal extension in the CD direction, but other configurations could be envisaged, for example partial zones in the form of a circular disc or in any other form, identical to one another or not, spaced apart from one another being surrounded by a complete weld zone, or spaced apart from the complete weld zone and isolated from the latter.

Figure 2B:
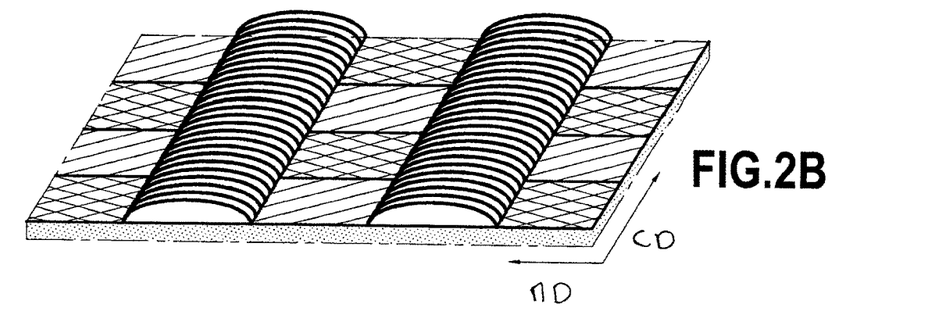

According to another embodiment shown in FIG. 2B, the alternation in the CD direction is supplemented by an alternation in the MD direction so as to thus form a sort of checkerboard between the partial and the complete weld zones.

Figure 2C:
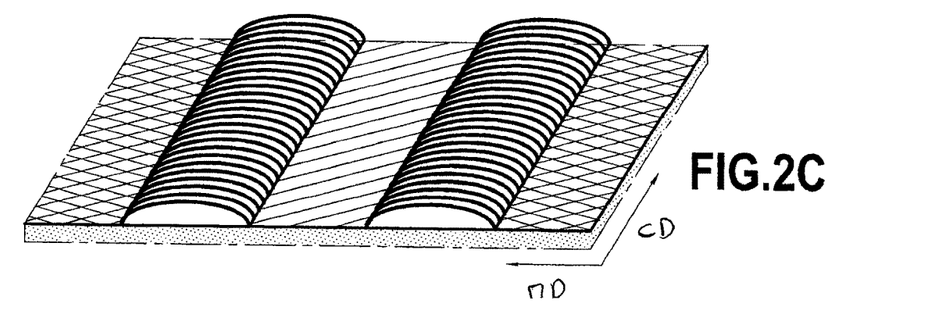

According to another embodiment shown in FIG. 2C, the strips of partial and complete welds are continued in the CD direction, but alternate with one another in the MD direction.

Figure 2D:
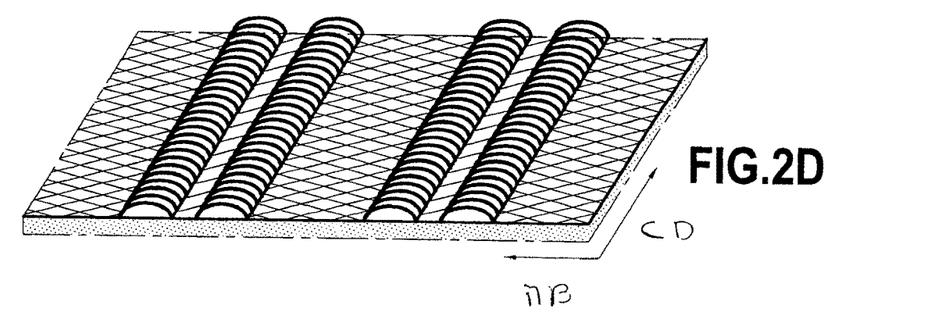

FIG. 2D shows another embodiment in which the complete weld strips have a greater width than partial weld strips formed alternately with the complete weld strips, the weld strips extending in the CD direction. In particular, the partial weld strips are thin, in particular to the point of being substantially in the form of a single weld line.

Figure 2E:
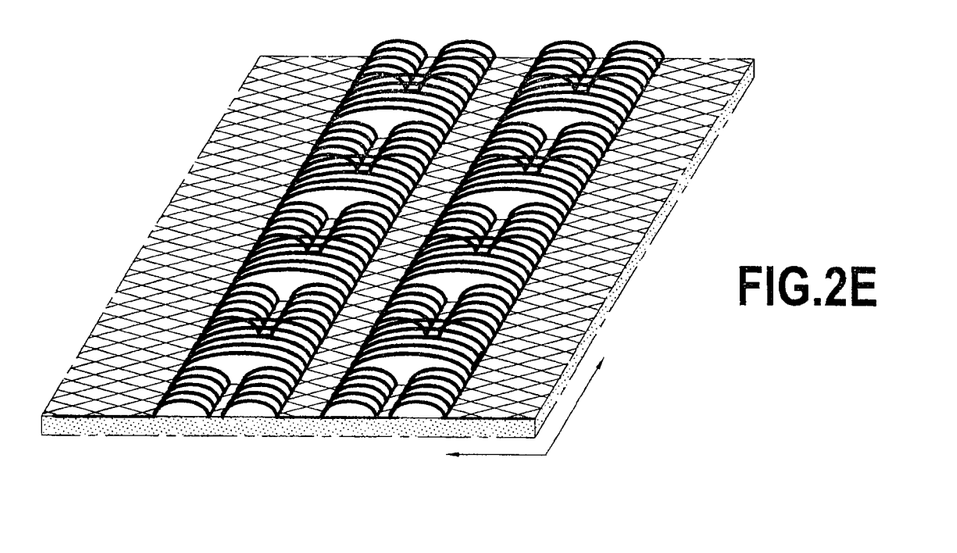

FIG. 2E shows an embodiment substantially identical to that of FIG. 2D, the only difference being that the partial weld lines are, furthermore, discontinuous in the CD direction.

Figure 2F:
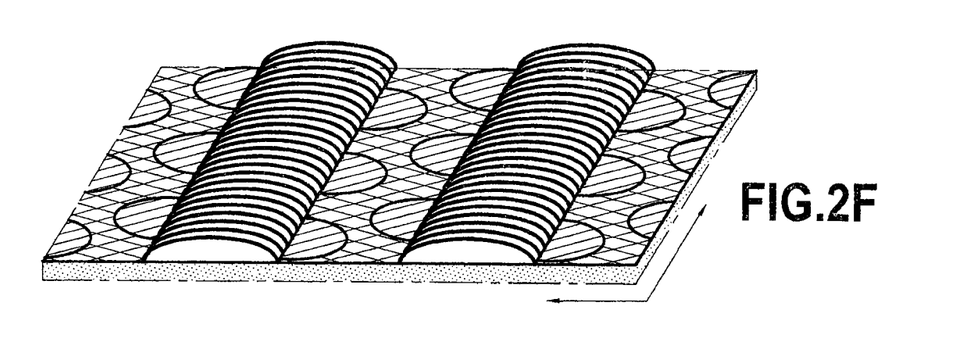

FIG. 2F shows an embodiment in which the partial weld zones are produced in the form of rows of zones in a semi-circle, spaced apart from one another in the CD direction, the rows of semi-circles preferably being, moreover, offset from one another from one row to the next, for example by a half distance between two successive semi-circles of a same row. Furthermore, the line forming the diameter of the semi-circle of a row is located on the side of the looped zones. In particular, as shown in the figure, the concavities of the semi-circles are orientated in opposite directions from one row to the next row.

Figure 2G:
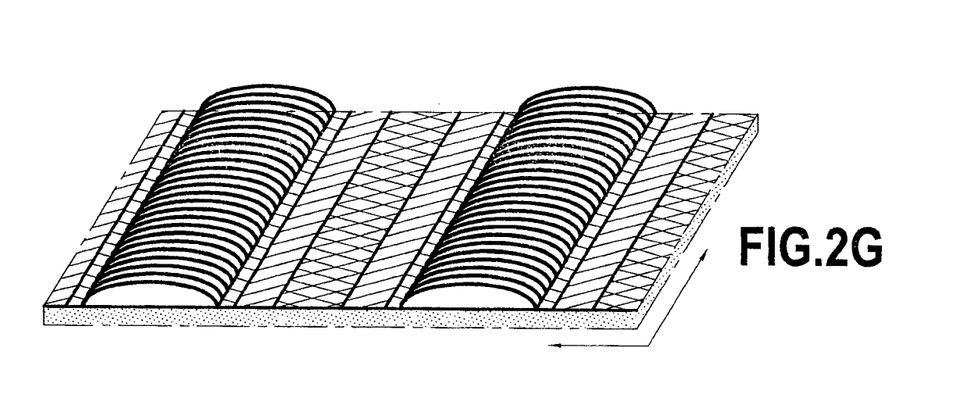
FIG. 2G shows diagrammatically a laminate according to the invention in order to illustrate the concept of side effect zone of the zones with a partial weld, a side effect that should be taken into account in particular when assessing the volume fraction of a partial weld zone by removing these side effect zones of the measurement zone.
Figure 2H:
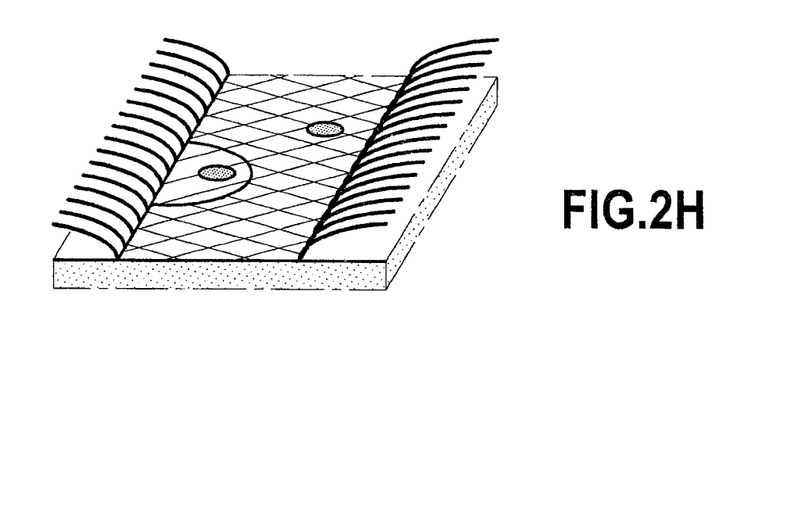
FIG. 2H shows diagrammatically a laminate similar to the one in FIG. 2F in which the measurement zones of the volume fraction or compactness have been shown.

FIG. 2H shows an embodiment similar to that of FIG. 2F in which the zones for measuring the volume fraction or compactness were shown. The measurement zones are indicated by substantially circular shapes with cross-hatching, respectively in the partial weld zone in the form of a half disc and in the complete weld zone.

FIG. 2G shows an embodiment in which two rows of loops are separated by a weld zone. The weld zone comprises a region in the form of a central complete weld strip (extending longitudinally in the CD direction), between two lateral partial weld zones, each separating the central complete weld strip of a respective row of loops. In each of the lateral partial weld zones a so-called side effect strip is moreover defined in which the weld is neither complete nor truly partial and corresponds to side effects that appear during calendering of the complete zone and partial zones respectively. The partial weld zone extends beyond these side effect zones, and to the contiguous row of loops.

When measuring the volume fraction one can, for the partial weld zones, take into account these side effect zones by removing them from the measured zone. One can do this in all of the embodiments described here, and also generally for any other similar embodiment.

In the different embodiments shown above fibers and/or filaments (these two terms are used in the present application in an equivalent and interchangeable manner) have been shown which are not consolidated with one another. However, one could also make provision to use consolidated filaments together in a non-woven fabric and make the respectively partial and complete welds on this non-woven fabric.

In the present application non-woven fabric means a product obtained at the end of the formation of a layer of fibers and/or filaments which have been consolidated. The consolidation can be mechanical, chemical or thermal and is manifested by the presence of connections between the fibers and/or the filaments. This consolidation can be direct, i.e. made directly between the fibers and/or filaments by welding, or it can be indirect, i.e. by means of an intermediate layer between the fibers and/or the filaments, for example a layer of adhesive or a layer of binder. The term non-woven relates to a structure in the form of a layer or strip of fibers and/or filaments which are interlaced in a non-uniform, irregular or random manner. A non-woven fabric can have a single layer structure or a multiple layer structure. A non-woven fabric can also be joined to another material such as a film in order to form a laminate. A non-woven fabric can be made from different synthetic and/or natural materials. The natural materials are, for example, cellulose fibers such as cotton, jute or paper pulp and the like, and can also include reprocessed cellulose fibers such as rayon or viscose. The natural fibers for a non-woven fabric can be prepared by using various processes such as carding. Synthetic materials include, but are not restricted to, for example, synthetic thermoplastic polymers which are known to form fibers that include, but are not restricted to, polyolefins, for example polyethyelene, polypropylene, polybutylene and the like; polyamide, for example polyamide 6, polyamide 6.6, polyamide 10, polyamide 12 and the like; polyesters, for example polyethylene teraphthalates, polybutylene terephthalates, polylactic acids and the like, polycarbonates, polystyrenes, thermoplastic elastomers, polymer vinyls, polyurethanes and mixtures and copolymers of the latter.

FIGS. 3A, 3B, 4A, 4B, 5 and 6 show in a top view (3A, 3B, 4A, 4B) or in cross-section (5, 6), respectively in the form of photographs and of diagrams of the parts of a non-woven fabric with loops in which complete calendering zones (FIGS. 3A, 3B and 6) and partial calendering zones (FIGS. 4A, 4B and 5) have been formed.

Figure 3A:
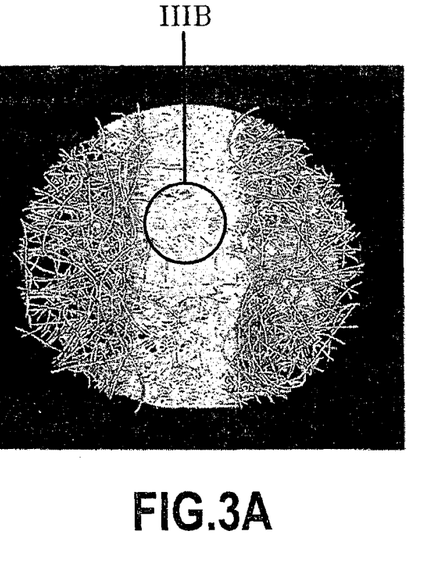
FIG. 3A is a photograph seen from above with a microscope (×50 enlargement) of a circular zone of a laminate comprising a complete weld zone (in the middle) between two regions with loops (on the left and on the right of the figure)
Figure 3B:
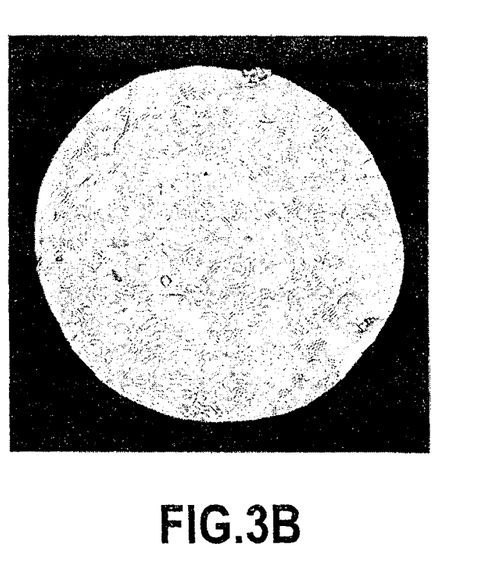
FIG. 3B is a view on a scale four times greater (×200 enlargement) of the circled part of the complete weld zone of FIG. 3A.

In the complete calendering zones—the zone delimited by the circle C in FIG. 3A and shown in FIG. 3B—the majority of the fibers and/or filaments have been crushed and cannot be differentiated from one another, such that the zone is mainly covered by an opaque field. In this zone the fibers have been greatly flattened. As can be seen in the cross-section in FIG. 5, the volume fraction is high, very little empty space remaining in the material of the fibers that have been welded together.

Figure 4A:
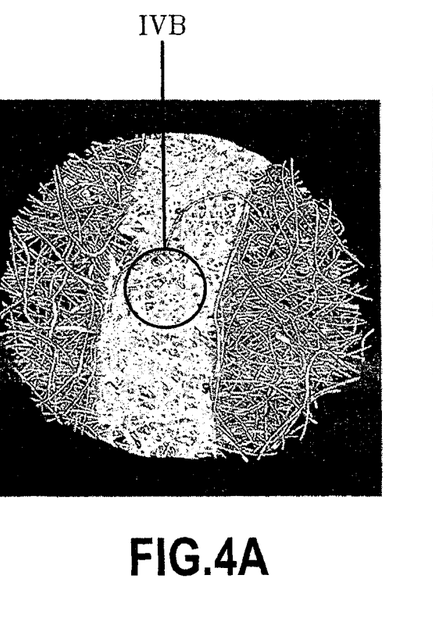
FIG. 4A is a photograph seen from above with a microscope (×50 enlargement) of a circular zone of a laminate comprising a partial weld zone (in the middle) between two regions with loops (on the left and on the right of the figure)
Figure 4B:
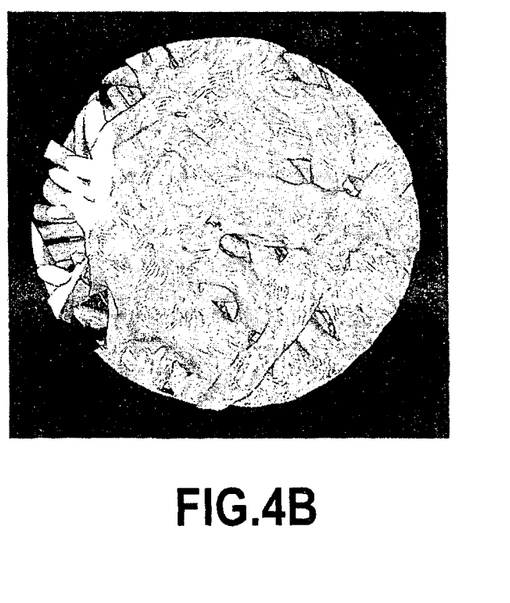
FIG. 4B is a view on a scale four times greater (×200 enlargement) of the circled part of the partial weld zone of FIG. 4A.
Figure 5:
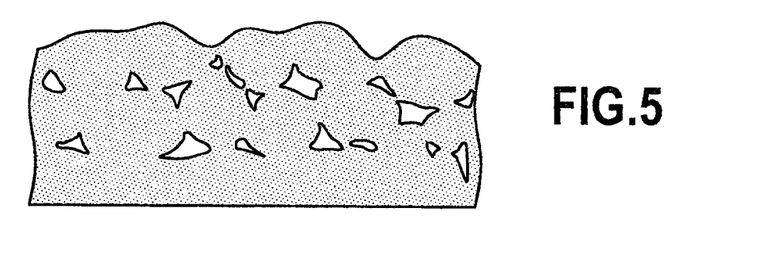
FIGS. 5 and 6 are views in diagrammatic form of a cross-section obtained by software when measuring the volume fraction, respectively for the weld zones of FIGS. 3B and 4B.
Figure 6:
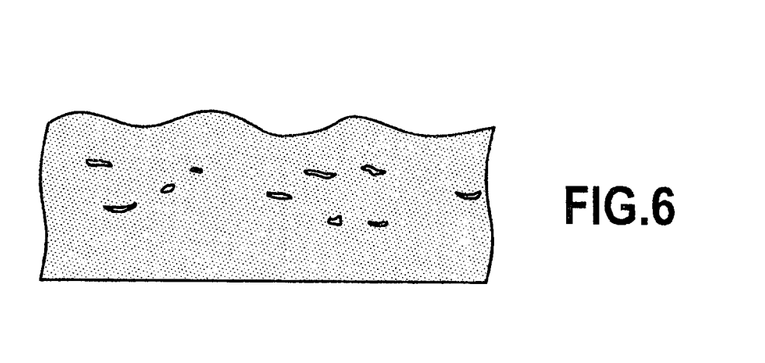

In the partial calendering zones, in particular the zone delimited by the circle B in FIG. 4A and shown in FIG. 4B, the majority of the fibers and/or filaments have only been slightly crushed and can be differentiated from one another. As can be seen in the cross-section in FIG. 6, the volume fraction is smaller than in FIG. 5, an empty space (i.e. without any material) that is not negligible remaining in the material of the fibers that have been welded together.

Different materials could be used for the fibers and/or filaments intended to be welded or attached completely and for the fibers and/or filaments intended to be welded or attached partially.

For a laminate, the MD direction (Machine Direction) is the direction in which the laminate is unrolled when it is produced and the CD direction (Cross Direction) is the direction perpendicular to the MD direction in the plane of the laminate.

According to one embodiment of the invention, one could envisage more than two types of weld, for example three types of weld.

According to embodiments, one could envisage different partial welds by varying their dimensions, their form, their volume fraction, thus making it possible to obtain the required performance for each type of application.

A product with alternating partial welds and complete welds in CD of the type of FIG. 2A makes it possible to obtain an increase of approximately 10% of the peel away performance with respect to the prior art. On thus obtains an average peel away force of 4.1 N as opposed to 3.7 N for a product made purely with complete welds.

Non-woven fabric with loops means a non-woven fabric that forms loops after being joined to the support.

In general, the fibers and the filaments differ mainly by their length and by their production method.

Filaments mean the unitary elements, with very great lengths with respect to the diameter to which their section is assigned, extruded continuously in order to directly form a strip of non-woven fabric that can then be consolidated by thermo-linking or any other means so as to make it possible to achieve the desired performance and/or their transportation. Preferably the filaments exhibit a length greater than 120 mm.

Fiber is understood to be the generic term designating a textile material or a textile material element with reduced length less than the length of the filaments and able to be spun and/or used in the production of non-woven fabrics. A distinction can be made between two types of fiber—the short fibers formed discontinuously with a small length of less than 70 mm (preferably 25 mm to 60 mm) and the long fibers formed discontinuously with a large length of greater than 70 mm (preferably 80 mm to 120 mm).

Unlike filaments that are consolidated directly after having been extruded, fibers are generally aligned and organized in a layer during a carding step that is well known to the person skilled in the art. This layer can then be consolidated by thermal linking or by any other means so as to make it possible to achieve the desired performance and/or their transportation.

The invention claimed is:

1. A looped layer in the form of a laminate comprising an internal support element (1), formed by at least one non-woven fabric, and a plurality of fibers and/or filaments (3) secured to an external face of the support element so as to form loops for engaging with hooks, said plurality of fibers and/or filaments (3) being secured to said external face in at least one attachment region, while in at least one other so-called looped region the filaments and/or fibers are not secured to the support element so as to thus form loops, characterized in that in at least one zone (5) of the at least one attachment region said plurality of fibers and/or filaments (3) are secured in a partial manner to said external face, while in at least one other zone (4) of the at least one attachment region said plurality of fibers and/or filaments (3) are secured to said external face in a complete manner.

2. The layer according to claim 1, characterized in that said plurality of fibers and/or filaments (3) are secured to said external face in both said at least one zone and said at least one other zone by welding.

3. The layer according to claim 2, characterized in that it exhibits a weld differential greater than 1.5.

4. The layer according to claim 1, characterized in that the plurality of fibers and/or filaments (3) forming the loops (7) are consolidated into at least one non-woven fabric.

5. The layer according to claim 1, characterized in that at least one layer of printing ink intended to form a pattern or patterns or designs is deposited onto the support element (1).

6. The layer according to claim 5, characterized in that said at least one zone and said at least one other zone alternate both in a CD direction along a given strip and in the MD direction of a strip to an adjacent strip.

7. The layer according to claim 1, characterized in that the at least one attachment region is/are made in the form of strips extending in a CD direction of the laminate, said at least one zone and said at least one other zones being produced alternately along a strip in the CD direction.

8. The layer according to claim 1, characterized in that said at least one other zone are made alternately in a MD direction of a strip to an adjacent strip.

9. The layer according to claim 1, characterized in that said at least one zone and said at least one other zone are made in the form of a semi-circle of which the diameter is contiguous to a looped region.

10. The layer according to claim 1, characterized in that said plurality of fibers and/or filaments (3) are secured to said external face in both said at least one zone and said at least one other zone by calendaring.

11. The layer according to claim 1, characterized in that the at least one attachment region is/are made in the form of strips extending in a CD direction of the laminate parallel to one another, said at least one zone and said at least one other zone being produced alternatively along a strip in the CD direction.

12. A diaper comprising a layer according to claim 1.

13. A diaper according to claim 11, characterized in that the layer forms a landing zone of the diaper.

14. A self-fastening closure system comprising on the one hand a loop element comprising a layer according to claim 1 and on the other hand a hook element, the hooks of which are arranged to be able to engage in the loops in order to provide the closure.

\* \* \* \* \*